United States Patent [19]

Gordon

[11] Patent Number: 5,167,921
[45] Date of Patent: Dec. 1, 1992

[54] LIQUID AND GAS SEPARATION SYSTEM

[75] Inventor: Lucas S. Gordon, Woodlands, Tex.

[73] Assignee: Baxter International Inc., Deerfield, Ill.

[21] Appl. No.: 795,170

[22] Filed: Nov. 19, 1991

Related U.S. Application Data

[60] Division of Ser. No. 664,449, Feb. 28, 1991, Pat. No. 5,110,549, which is a continuation of Ser. No. 489,760, Feb. 27, 1990, abandoned, which is a continuation of Ser. No. 59,064, Jun. 5, 1987, abandoned, which is a continuation-in-part of Ser. No. 885,963, Jul. 14, 1986, abandoned.

[51] Int. Cl.$^5$ .............................................. A61M 1/14
[52] U.S. Cl. ....................................... 422/45; 422/46; 422/47; 128/DIG. 3; 261/DIG. 28; 55/178; 55/488; 55/87; 210/321.62; 210/349; 210/492; 210/500.24
[58] Field of Search ..................... 422/46, 47, 45; 128/DIG. 3; 261/DIG. 28; 210/321.62, 188, 436, 488, 492, 472, 349, 500.24; 55/178, 486, 488, 87

[56] References Cited

U.S. PATENT DOCUMENTS

| | | | |
|---|---|---|---|
| 4,073,622 | 2/1978 | Luppi | 422/47 |
| 4,138,464 | 2/1979 | Lewin | 422/47 X |
| 4,140,635 | 2/1979 | Esmond | 422/47 X |
| 4,158,693 | 6/1979 | Reed et al. | 422/47 X |
| 4,188,360 | 2/1980 | Kurata | 422/47 X |
| 4,261,951 | 4/1981 | Milev | 422/47 X |
| 4,336,224 | 6/1982 | Siposs | 422/47 X |
| 4,424,190 | 1/1984 | Mather, III et al. | 422/48 X |
| 4,440,723 | 4/1984 | Gordon | 422/47 |
| 4,490,331 | 12/1984 | Steg, Jr. | 422/48 X |
| 4,585,056 | 4/1986 | Oscarsson | 422/46 X |
| 4,637,917 | 1/1987 | Reed et al. | 422/46 |
| 4,698,207 | 10/1987 | Bringham et al. | 422/48 X |

FOREIGN PATENT DOCUMENTS 0122748 10/1984 European Pat. Off. .

*Primary Examiner*—Lynn M. Kummert
*Attorney, Agent, or Firm*—Bruce M. Canter; Raymond Sun

[57] ABSTRACT

A defoaming device for separating foam and bubbles from a liquid, such as blood, is disclosed. The device can be used in conjunction with a medical device, such as a membrane oxygenator, for separating air from blood while minimizing blood contact with the antifoam agent used in the device. In a first embodiment, the device includes a reservoir and a filtering material that does not contain any antifoaming agent. This filtering material is positioned in a lower portion of the reservoir to separate foam and bubbles from the liquid. An element containing an antifoaming agent is positioned in the reservoir above the maximum surface fluid level therein and receives the foam and bubbles that rise from the filtering material. Contact of the liquid with the antifoaming agent is substantially avoided. In a second embodiment, an element containing an antifoaming agent is positioned in the reservoir within the fluid therein.

19 Claims, 3 Drawing Sheets

LIQUID AND GAS SEPARATION SYSTEM

BACKGROUND OF THE INVENTION

This application is a divisional of U.S. application Ser. No. 07/664,449, filed Feb. 28, 1991, now U.S. Pat. No. 5,110,549, which is a continuation of U.S. application Ser. No. 07/489,760, filed Feb. 27, 1990, now abandoned, which is a continuation of U.S. application Ser. No. 07/059,064, filed Jun. 5, 1987, now abandoned, which is a continuation-in-part of U.S. application Ser. No. 06/885,963 filed on Jul. 14, 1986, now abandoned.

I. FIELD OF THE INVENTION

This invention relates to a system useful for the separation of liquid and gas, and more particularly to a medical device, such as a blood oxygenator or a cardiotomy reservoir, which employs a defoamer system that, in one embodiment, affords excellent separation of macroscopic and microscopic air from blood while at the same time minimizing blood path contact with the silicone containing compounds typically used in the defoamer.

II. DESCRIPTION OF THE PRIOR ART

There are many systems known in the art which are used to remove gas (such as air) from fluids and which also employ a defoamer assembly in such systems. For example, in various types of surgical procedures, it is often necessary to perform a treatment whereby the patients blood is subject to a bypass flow outside of the patient's body, and an apparatus such as an oxygenator is employed. In many such oxygenators, oxygen is transferred to the blood via a procedure which forms a foam and therefore requires a defoamer assembly.

These oxygenators are used in open-heart surgery and other operations and treatments of the body when it is necessary to establish an extracorporeal circulation system for temporarily assuming the functions of the heart and lungs of the patient. In such a system, the oxygenator operates to perform the function usually performed by the lungs of the patient, i.e., the life-supporting transfer of oxygen into the blood and carbon dioxide out of the blood. The oxygenator is used in association with a pump which performs the function of the heart to cause circulation of the blood. Thus, early versions of the oxygenator were often referred to as "heart-lung" machines. The early heart-lung machines were typically rotating discs which passed through a pool of blood, but were only partially immersed therein such that the free surface of the disc exposed the blood to oxygen and accomplished some gas transfer. After this, bag-type oxygenators were introduced which were superior to the disc oxygenators, but which left much to be desired.

At the present time two principal types of blood oxygenators are used which have proven highly efficient, provide minimal blood trauma, are convenient to set up and operate, are cost effective and have provided excellent clinical results, i.e. bubble oxygenators and membrane oxygenators. In a membrane oxygenator, a thin, highly gas permeable membrane is placed between the gas and blood. Venous blood flows along one side of the membrane and gas is on the other side. A pressure gradient is established so that when the partial pressure for oxygen is higher in the ventilating gas than the partial pressure for oxygen in the venous blood, oxygen will diffuse across the membrane into the blood. Bubble oxygenators simply diffuse gas bubbles into venous blood. The oxygenated blood is typically defoamed before it is ready for delivery to the patient.

In medical devices such as the oxygenators as described above, and in other medical devices such as cardiotomies and hardshell venous reservoirs, air or some other gas can be introduced into the blood, e.g. oxygen (in an oxygenator), nitrogen, carbon dioxide, etc. Typically, when this occurs it is medically necessary to remove certain gas from the blood prior to the blood going to the patient. Separation of the blood from the gas requires the medical device to be used in combination with a defoaming device which typically incorporates some sort of an agent to assist in breaking the foam down. In medical applications, about the only agent that has proved acceptable is a silicone antifoam agent. However, in the process of the silicone agent performing its job, i.e. remove the gas from the blood, a small amount of the silicone actually is transferred into the blood. The problem with this is that silicone is not metabolized by the human body, and therefore silicone accumulates in the body. Even though silicone is an inert material it is undesirable within the human body, under some circumstances, because it can tend to clog up some of the very small capillaries and arteries within the human body.

As described herein, the features of the present invention can be employed in various types of medical devices. Examples of the type of so-called membrane oxygenators which can employ the features of the present invention are described in U.S. Pat. Nos. 4,094,792 and 4,196,075 both of which are assigned to Bentley Laboratories, Inc., the assignee of the present invention. In addition Bentley Laboratories, Inc. products identified as the Bentley BCM-3 and BCM-7 integrated membrane oxygenators which are oxygenators having three major components can incorporate the defoamers of the present invention. Examples of the bubble type blood oxygenator that can employ the features of the present invention are described in U.S. Pat. Nos. 3,468,631, 3,488,158 and 3,578,411, the last two of which describe devices which have come to be known as the Bentley Oxygenator, and also U.S. Pat. Nos. 4,282,180 and 4,440,723, both assigned to Bentley Laboratories, Inc.

Various prior art examples of blood oxygenators and gas-liquid type of transfer apparatus are described in U.S. Pat. Nos. 3,065,748; 3,256,883; 3,493,347; 4,073,622; 4,138,288; 4,182,739; 4,203,944; 4,203,945; 4,288,125; 4,231,988; 4,272,373; 4,336,224; 4,370,151; 4,374,088; 4,396,584; 4,407,777; 4,440,722; 4,493,692 and 4,533,516.

SUMMARY OF THE INVENTION

It is therefore an object of the present invention to provide an improved liquid and gas separation system and further to provide a device for separating gas from liquid which is substantially devoid of the above-noted disadvantages.

Another object of the present invention is to provide a defoaming device which has particular use with a medical device such as an oxygenator for the removal of gases, such as oxygen, from blood.

Still another object of the present invention is to provide a defoaming device which employs a silicone antifoam agent to assist in breaking the foam (bubbles) in the blood down, and which at the same time substantially avoids contaminating the blood with undesirable silicone.

Still another object of the present invention is to provide a defoaming device for separating gases from blood which employs a silicone antifoam agent and in which the blood contacts the silicone antifoam agent only when there is gas in the blood.

The foregoing and other objects are accomplished in accordance with the features of the present invention. In a first embodiment, the objects are accomplished by providing a defoaming device for separating gas in the form of foam from the liquid and then breaking the foam down into a liquid and a gas. The device comprises a reservoir and a filtering element that does not contain an antifoaming agent and which is positioned in the lower portion of the reservoir to first contact the liquid and separate gas foam and bubbles from the liquid. Positioned in the reservoir above the maximum fluid level is an element containing an antifoaming agent which then comes in contact with the foam that rise from the filtering element and breaks down the foam.

Basically, when blood is moving through a medical device it may from time to time have some gas in it. When gas is in the blood, and it's desired to remove it, an antifoam agent such as a silicone material (e.g. simethicone) is typically used. However, it is preferred not to have the blood directly contact the silicone material. The defoamer device in accordance with the features of the present invention is unique in that when in operation, blood without gas will not contact the silicone containing material. Foam, macroscopic bubbles, and microscopic bubbles, appearing in the blood will be separated from the blood without contacting the silicone antifoam agent. Then, after separation, the foam and bubbles are allowed to travel to a portion of the defoamer assembly positioned above the maximum level of blood in the assembly's reservoir where the foam and bubbles are then placed in contact with an antifoam dipped material. Thus, the only thing that contacts the antifoam agent is the foam or bubbles that rise up to the area above the blood level where the antifoam agent is located. The present invention is unique because it defines a defoamer which allows selective exposure of only the foam and bubbles to an antifoaming agent.

In a second embodiment of the invention, a defoaming device having a somewhat different approach is provided for separating and breaking down foam and bubbles from a liquid. The device in this case is very similar in general construction to the above described first embodiment except that the defoaming agent is contained in the lower portion of the reservoir to contact the liquid and separate and break up gas, foam and bubbles from the liquid. In the second embodiment, such as when used in a medical device with blood, the blood will come directly in contact with the silicone material, but with the benefit of increased air removal from the blood.

BRIEF DESCRIPTION OF THE DRAWINGS

For a better understanding of the invention as well as other objects and further features thereof, reference is made to the following detailed disclosure of this invention taken in conjunction with the accompanying drawings wherein.

DESCRIPTION OF THE PREFERRED EMBODIMENTS

Broadly speaking, the defoaming device in accordance with the invention can be used for removing a gas, such as air, from various types of fluids, such as blood. The defoamer system as described herein is particularly suited for use in any open system device which requires air-blood separation. Excellent opportunities for using this defoamer system thereby exist in such medical devices as, for example, bubble oxygenators, membrane oxygenators, cardiotomies, hardshell venous reservoirs, blood autotransfusion systems and oxygenated blood cardioplegia systems. Thus, although the unique features of the defoaming device in accordance with the present invention will be described below with regard to its use in an oxygenator for the purpose of removing gas foam and bubbles from blood, it is to be understood that the defoaming device has broader use, does not require the particular structural features of the particular embodiment described herein and is capable of removing various gases from different liquids when used with a medical device and in other environments.

Figure 1:
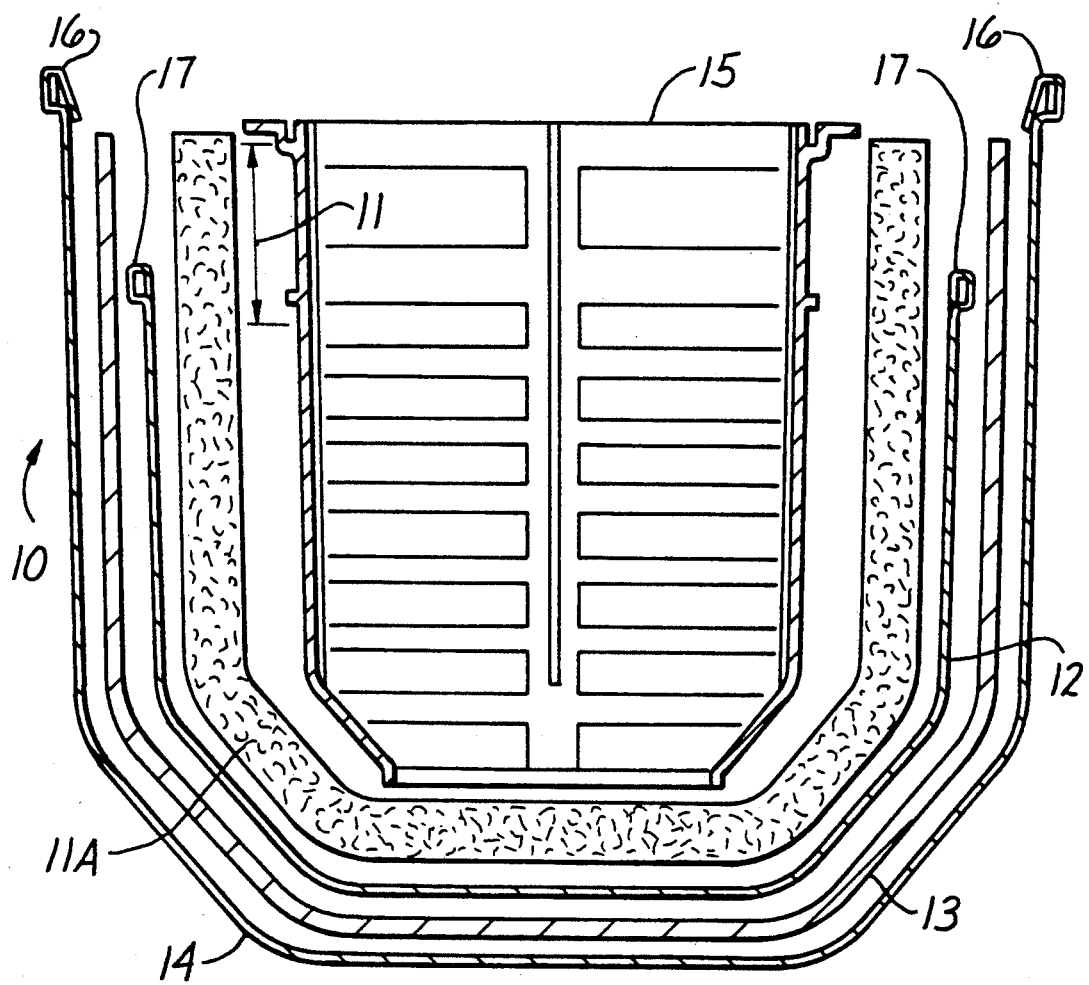
FIG. 1 is a plan sectional view of a defoaming apparatus illustrating the structural features thereof in accordance with the preferred embodiments of the first embodiment of the present invention.

The basic features of a first embodiment of the defoaming device 10 of this invention are shown in FIG. 1. The device illustrated can be identified as either the Bentley Laboratories, Inc. BCM-3 or BCM-7 defoamer which can be used, for example, in either the Bentley BCM-3 or BCM-7 integrated membrane oxygenator as described in commonly assigned and copending Ser. No. 885,207, filed Jul. 14, 1986, entitled "Integrated Membrane Oxygenator, Heat Exchanger and Reservoir" or in the Bentley BMR-1500 membrane oxygenator reservoir now U.S. Pat. No. 4,698,207. The defoamer device 10 is a three-piece assembly which affords excellent separation of foam and macroscopic and microscopic air from blood while minimizing blood path contact with the silicone containing antifoam compound that is employed in the device. The three primary components of the defoamer device 10 shown in FIG. 1 are as follows: (a) A low antifoam dipped (only on the top portion thereof 11,) polyurethane, thermally reticulated (open cell), foam pre-stage 11A constructed, for example, from ⅛ inch thick, 100 ppi (pores per inch) polyurethane; (b) a screen 12 which can be a heparin coated 50 micron (mesh opening in microns) polyester screen having a 36 percent open area (twill weave); and (c) a foam spacer stage 13 which can be a 150 inch thick, 15 ppi polyurethane, thermally reticulated (open cell) foam spacer stage.

The polyurethane foam pre-stage 11 is the only element of defoamer device 10 which includes an antifoaming agent. In accordance with the features of this invention an antifoam compound (e.g. simethicone) is applied to the low antifoam defoamer element 11A only along a relatively narrow border 11, e.g. a two inch border, measured from the top portion of defoamer 10 (Note, 11 and 11A are the same piece of foam material).

It is this low antifoam design which presents an antifoam coated surface only to the target blood foam and bubbles which, since being buoyant, move to the top of the blood. Thus contact between the blood and the silicone coating antifoam agent is minimized i.e. contact occurs with the foam and bubbles and the antifoam agent above the maximum liquid surface level of the blood. When defoaming device 10 is employed in an oxygenator, during normal operation the maximum blood column height within the defoamer remains below the lower margin area of the element 11 which contains the antifoam material. Microbubbles are not significantly affected by the simethicone compound or other antifoaming agents and exposure of the whole blood path to the antifoaming agents is unnecessary. The defoaming device 10 allows selective exposure of only blood foam to an antifoaming agent.

The 100 ppi polyurethane foam pre-stage 11A acts to filter foam, macroscopic air bubbles and microscopic air bubbles appearing in the blood before its presentation to the heparin coated polyester microscreen 12. Although the microscreen 12 is capable of removing the macroscopic air which is first presented to the pre-stage polyurethane foam 11, doing so causes an occlusive air film to form on the screen. Exposure of microscreens to large amounts of macroscopic air decreases their effective surface area and can impede their ability to pass fluids, even when treated with wetting agents such as heparin. A possible consequence of air occlusion of these microscreens is that blood passing through the diminished screen area is subjected to increased flow resistance and pressure drop. These increases may produce blood formed elements damage. Placement of a polyurethane foam "filtering stage" prior to the heparin coated screen significantly improves the blood air elimination as well as the blood handling capability of the defoamer assembly.

After blood passes through the 100 ppi pre-stage 11, it comes into contact with the 50 micron heparin dipped polyester screen 12. This screen effectively eliminates microbubbles greater than 50 micron in diameter. Although polyester microscreen fabrics are available with smaller mesh openings which would provide even greater air filtration, these fabrics would present certain disadvantages. As the fabric's mesh opening size decreases, the percent open area of the fabric (the effective blood passage area) decreases significantly. As the percent open area decreases, the blood is subjected to greater resistances and shearing forces. Increased shearing forces are reflected in greatly increased blood damage. The 50 micron PES twill heparin dipped screen provides excellent microbubble filtration in concert with a relatively high 36 percent open area. In-vitro evaluation of prolonged blood flow through this screen has clearly demonstrated the excellent blood handling capability of this material.

As illustrated in FIG. 1, the heparin coated microscreen 12 does not enclose the upper portion of the polyurethane foam 11. During normal operation of the defoaming device 10, the blood level within the defoamer will always be below the margin of the polyester microscreen. Should the screen 12 become occluded, the blood level within the defoamer will exceed the height of the screen and blood flow will bypass the screen. All blood flow will pass through the antifoam treated section of the polyurethane defoamer 11 and cascade over the occluded microscreen. This integral bypass feature of the defoamer assembly 10 is a crucial safety feature which allows the use of a microscreen in the blood path without the threat of total blood path occlusion concommitant with screen occlusion.

The third element of the defoamer assembly 10 is a spacer stage 13 which is preferably a ⅛ inch thick 15 ppi polyurethane, thermally reticulated (open cell) material. This element is a spacer stage which prevents the wicking of blood between the polyester microscreen 12 (or the upper segment of the 100 ppi prestage 11) and the outer containment layer, e.g. a polyester tricot stock, in which the elements of the defoamer assembly are enclosed. A large pore material, such as a 15 ppi polyurethane material 13 is preferably used for this spacer stage to limit material surface area for air and blood remixing.

All three elements 11A, 12, and 13 are preferably located in a polyester tricot sock 14 outer layer and the entire defoaming assembly is secured onto a rigid vented support grid 15. The sock 14 and screen element 12 are connected to straps at positions 16 and 17 in the manner as described herein below, i.e. the example given of how the defoaming assembly 10 can be used in a membrane oxygenator.

In accordance with the features of the particular embodiment of the defoamer assembly that has been described herein above, there are certain critical parameters which will enable the defoamer assembly to operate in the environment of an oxygenator, particularly a membrane oxygenator, in an efficient manner. In defoamer assembly 10, the polyurethane foam 11, 11A and 13 and polyester screen 12 pore sizes are critical to the efficient functioning of the entire assembly.

In the polyurethane thermally reticulated foam prestage elements 11 and 11A, a preferred pore size for the material is about 100 ppi and this pore size can range from about 80 to 110 ppi. It is preferred not to use foam for element 11 having a pore size less than about 80 ppi because this type of material will not adequately screen macroscopic air. If the pore size of element 11A is greater than about 110 ppi it may have too high a breakthrough volume thereby bringing the blood path in contact with antifoaming agents. In the polyester screen 12, a preferred pore size for the screen material is about 50 microns and can range from about 50 to 71 microns. It is preferred not to use a screen having less than about 50 micron openings because this type of microscreen has an inadequate percent of open area. A low percent of open area may produce unacceptable levels of blood damage. If the screen has greater than about 71 micron openings, it will exhibit little affect in reducing microbubble levels. In the polyurethane thermally reticulated foam spacer stage 13, a preferred pore size is about 15 ppi and this can range from about 15 to 25 ppi. It is preferred not to use a foam spacer stage 13 having a ppi less than about 15 ppi because it is difficult to manufacture defoamer material with this low pore size. Polyurethane foam material with a ppi greater than about 25 ppi is generally not acceptable because it presents too much material surface area for air/blood remixing.

Figure 2:
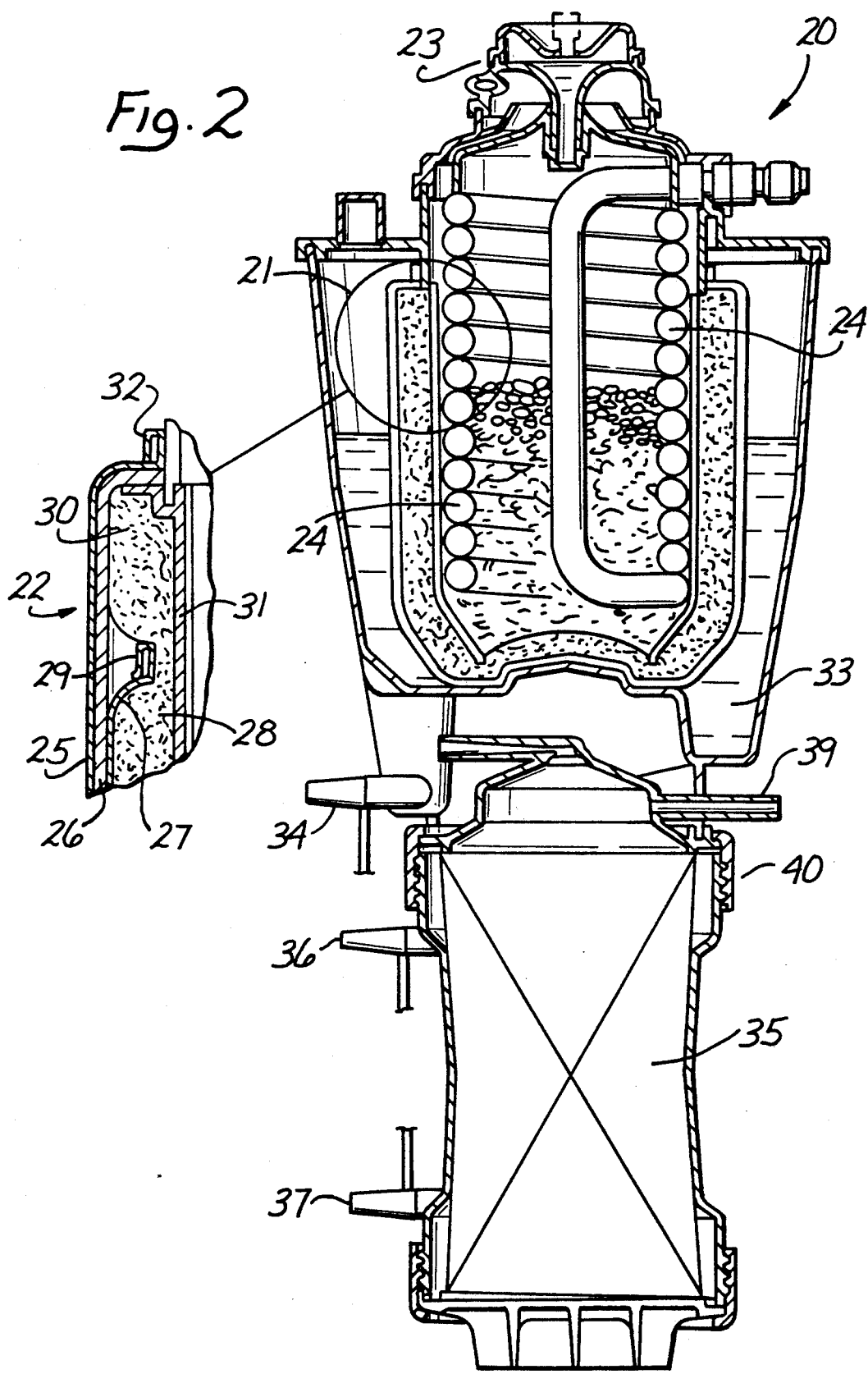
FIG. 2 is a plan sectional view of a membrane oxygenator and an enlarged portion thereof illustrating how a defoaming apparatus in accordance with the present invention can be used with the oxygenator.

The operation and use of the defoaming assembly as described herein above will now be described in the environment of a membrane oxygenator. As illustrated in FIG. 2, there is shown a membrane oxygenator 20 with the circled area 21 illustrating in an enlarged manner the structure of a defoaming assembly 22 incorporating the unique features of the present invention. In use, blood from a patient is fed into the membrane oxygenator through a venous inlet connector located at the top portion 23 of the oxygenator. Once in the oxygenator, the blood slowly trickles in a downward direction onto the heat exchanger tubes 24, which are preferably in the form of a helically wrapped tube, and then into the defoaming assembly 22. It should be noted that in the membrane oxygenator the purpose of passing the blood through the defoaming assembly is to separate incidental air that is fed into the oxygenator along with the blood.

The defoaming assembly 22 is structured of an outer layer of a polyester tricot sock 25. Located adjacent sock 25 is a layer 26 of a 15 ppi polyurethane foam material. A 50 micron polyester screen 27 is positioned between foam material 26 and layer 28 of 100 ppi polyurethane foam material. A strap member (not shown) is secured to screen 27 at position 29 and used to squeeze foam layer 28 inwardly (as shown) at the approximate location of the maximum blood level within the defoaming assembly. The 100 ppi polyurethane foam material 30 positioned above this indented portion of the 100 ppi foam (i.e positioned above the maximum surface of the blood level within the defoaming assembly) is the portion of the 100 ppi foam material which includes an antifoaming agent such as, for example, simethicone. The next illustrated layer of defoaming assembly 22 represents a support grid 31. Another strap element is secured to the sock 25 at position 32 and holds the sock onto the support grid.

During use of the membrane oxygenator 20, the blood travels from the heat exchange tubes 24 and is directed into contact with the 100 ppi polyurethane foam prestage 28 (that part of the 100 ppi foam without the antifoaming agent) which acts to filter foam, macroscopic air bubbles, and microscopic air bubbles appearing in the blood. Afterwards the blood travels to the heparin coated polyester microscreen 27 which effectively eliminates the microbubbles of air in the blood greater than 50 microns in diameter. The microbubbles separated from the blood and any other foam travel to the antifoam area 30 of the 100 ppi polyurethane foam which is located above the maximum surface level of the blood when the separation of the air from blood occurs. Thus, the defoamer allows selective exposure of only blood foam (bubbles) to the antifoaming agent.

After the blood passes through the defoaming assembly 22, it goes into a venous reservoir 33. Thereafter, the blood passes from the reservoir out of a venous reservoir outlet connector 34 to a pump (not shown) which pumps the blood back to the lower portion 40 of oxygenator 20 through an oxygenator blood inlet connector 39. It is in the lower portion 40 of the membrane oxygenator 20 where oxygen transfer to the blood actually occurs. After being pumped back into the oxygenator 20, the blood flows thru a plurality of vertical hollow fibers 35. The oxygenator 20 includes an oxygen inlet connector 37 which feeds the oxygen to fibers 35 and an oxygen outlet connector 36 which allows the oxygen to travel out of the oxygenator. Basically the blood flows through the fibers 35 while the oxygen flows around the hollow fibers whereby the oxygenation takes place.

Figure 3:
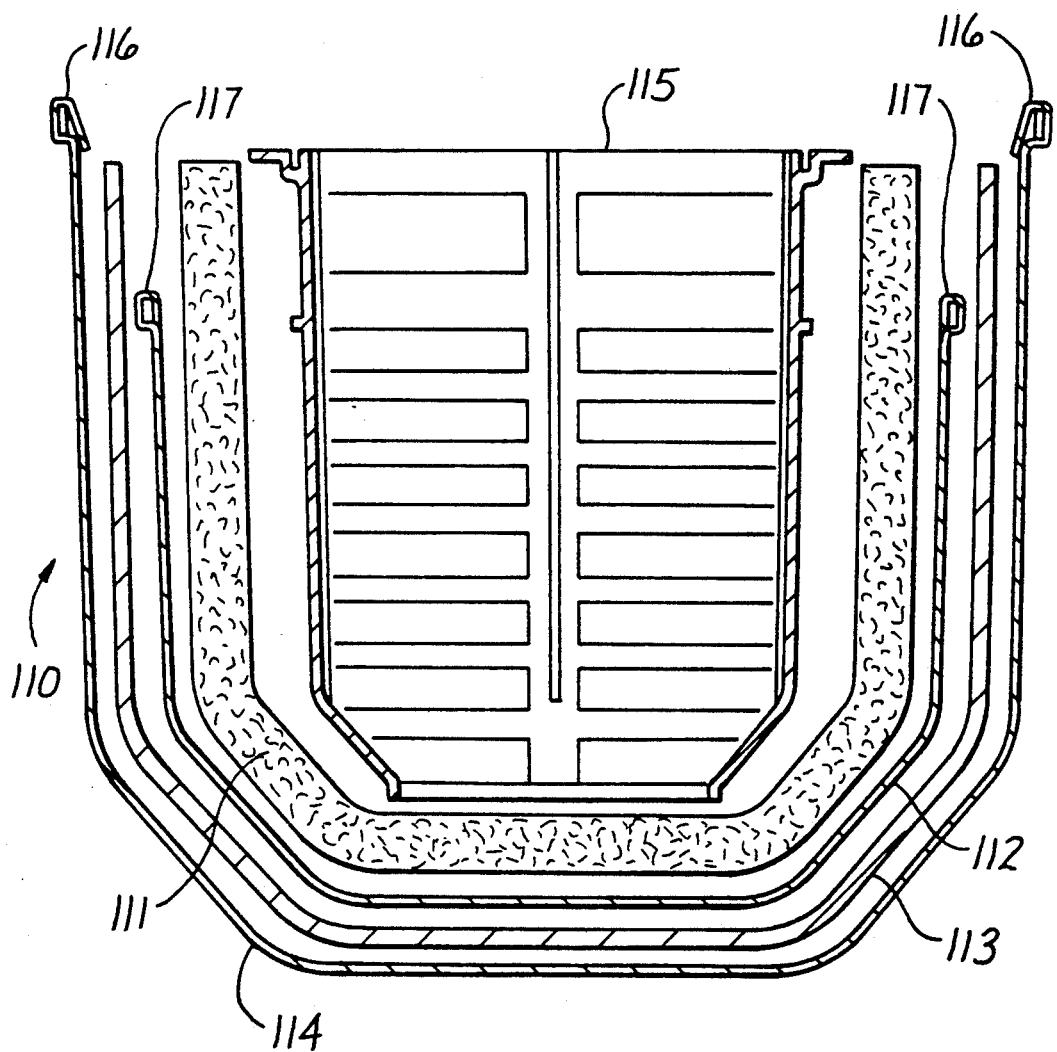
FIG. 3 is a plan sectional view of a defoaming apparatus illustrating the structural features thereof in accordance with the second embodiment of the present invention.

A second embodiment of the invention is shown in FIG. 3. The second embodiment is very similar in general construction to the first embodiment as shown in FIG. 1. However, in the second embodiment, the defoaming agent is also contained in the lower portion of the reservoir and contacts the liquid, or blood, in the reservoir. In addition, different ranges of pores per inch for the pre-stage and spacer stage and different ranges of mesh openings for the screen are used as compared to the first embodiment. The second embodiment is particularly useful when larger quantities of air must be removed from blood.

The defoamer device 110 is a three piece assembly. The first element is a low antifoam dipped polyurethane, thermally reticulated (open cell) foam pre-stage 111 constructed, for example, from approximately $\frac{1}{2}$ inch thick polyurethane. The antifoaming agent may be any suitable type such as simethicone which, for maximum effect, may be applied throughout pre-stage 111. In this case, all of the blood is exposed to the antifoaming agent. In the alternative, the antifoaming agent may be placed only on selected regions, such as in bands, of pre-stage 111, for instance, it may be placed from the top of pre-stage 111 and extend down into the liquid, or blood, area to some extent, but not necessarily be placed throughout pre-stage 111. It has been found in the device shown in FIG. 3 that superior air removal will be assured when the pore size of pre-stage 111 is from about 45 pores per inch (ppi) to about 110 ppi, the preferred range being about 50 ppi to about 75 ppi, and the most preferred size being approximately 65 ppi.

The second element is a screen 112 which can be coated with a wetting agent such as heparin and formed of polyester. It has been found in the device shown in FIG. 3 that the screen can have a mesh opening from about 30 microns to about 100 microns, the preferred range being from about 40 microns to about 60 microns, and the most preferred mesh opening being approximately 40 microns. Any suitable heparin coating may be used, three of which are benzylconium; "DUROFLO II" heparin coating sold by American Bentley of Irvine Calif.; and "TDMAC", tridodecylmethylammonium chloride bonded to heparin sold by Sherwood Medical Industries of St. Louis, Mo.

The third element is a foam spacer stage 113 which can be approximately 166 inch thick polyurethane, thermally reticulated (open cell) foam spacer stage. It has been found in the device shown in FIG. 3 that the spacer can have a pore size range of about 10 ppi to about 25 ppi, the preferred range being from about 10 ppi to about 20 ppi, and the most preferred size being approximately 15 ppi.

As illustrated in FIG. 3, screen 112 preferably does not enclose the upper portion of pre-stage 111 providing the same bypass feature as described in connection with FIG. 1 should screen 112 become occluded. All three elements 111, 112 and 113 are preferably located in a tricot sock 114 outer layer and the entire defoaming assembly is secured onto a rigid vented support grid 115. The sock 114 and screen element 112 are connected to straps at positions 116 and 117, in a manner similar to that described in conjunction with FIG. 1, and the defoaming assembly 110 can be used in an oxygenator, such as shown in FIG. 2.

The apparatus described in accordance with the present invention can be used to defoam numerous types of liquids. One example of a liquid is blood, which has been used as a specific example to describe a detailed embodiment of the present invention.

While this invention has been described in conjunction with specific embodiments thereof, it is evident that many alternatives, modifications and variations will be apparent to those skilled in the art. Accordingly, the present invention is intended to embrace all such alternatives, modifications and variations, as fall within the spirit and scope of the appended claims.

What is claimed is:

1. A method for separating foam and bubbles from a liquid comprising the steps of:
   providing a reservoir with a first filter element comprising an upper region and a lower region;
   providing a microscreen element about the lower region of the first filter element but not about the upper region of the first filter element;
   passing a liquid in the reservoir through the lower region of the first filter element to first separate the foam and bubbles from the liquid, wherein the liquid passed through the lower region subsequently passes through the microscreen element; and
   diverting the liquid through the upper region of the first filter element if the liquid flow through the microscreen element becomes blocked, wherein the diverted liquid flow bypasses the microscreen element.

2. The method of claim 1, wherein the upper region of the first filter element has a defoaming agent incorporated therein and the lower region of the first filter element is absent a defoaming agent.

3. The method of claim 2, further including the step of defoaming the separated foam and bubbles at the upper region of the first filter element.

4. The method of claim 3, wherein the liquid will not be exposed to the upper region of the first filter element if the liquid flow through the microscreen element does not become blocked.

5. The method of claim 4, wherein the liquid is blood and the foam and bubbles are formed by air.

6. The method of claim 5, wherein the defoaming agent comprises silicon.

7. The method of claim 5, wherein the defoaming agent comprises simethicone.

8. The method of claim 2, further including the step of coating the microscreen element with heparin.

9. The method of claim 2, further including the step of providing a second filter element about the microscreen element, wherein the liquid passing through the microscreen element will subsequently pass through the second filter element.

10. The method of claim 2, further including the step of coating portions of the lower region of the first filter element with the defoaming agent.

11. A method for separating foam and bubbles from a liquid comprising the steps of:
    providing a reservoir with a first filter element comprising an upper region having a defoaming agent incorporated therein and a lower region also having a defoaming agent incorporated therein;
    providing a microscreen element about the lower region of the first filter element but not about the upper region of the first filter element;
    passing a liquid in the reservoir through the lower region of the first filter element to first separate the foam and bubbles from the liquid, wherein the liquid passed through the lower region subsequently passes through the microscreen element; and
    diverting the liquid through the upper region of the first filter element if the liquid flow through the microscreen element becomes blocked, wherein the diverted liquid flow bypasses the microscreen element.

12. The method of claim 11, wherein the liquid will not be exposed to the upper region of the first filter element if the liquid flow through the microscreen element does not become blocked.

13. The method of claim 12, wherein the liquid is blood and the foam and bubbles are formed by air.

14. The method of claim 11, further including the step of coating the microscreen element with heparin.

15. The method of claim 11, wherein the defoaming agent comprises silicon.

16. The method of claim 11, wherein the defoaming agent comprises simethicone.

17. The method of claim 11, further including the step of providing a second filter element about the microscreen element, wherein the liquid passing through the microscreen element will subsequently pass through the second filter element.

18. A method for separating foam and bubbles from a liquid comprising the steps of:
    providing a reservoir with a first filter element comprising an upper region having a defoaming agent incorporated therein and a lower region;
    providing a microscreen element about the lower region of the first filter element but not about the upper region of the first filter element;
    coating the microscreen element with heparin;
    providing a second filter element about the microscreen element;
    passing a liquid in the reservoir through the lower region of the first filter element to first separate the foam and bubbles from the liquid, wherein the liquid passed through the lower region subsequently passes through the microscreen element and the second filter element;
    diverting the liquid through the upper region of the first filter element if the liquid flow through the microscreen element becomes blocked, wherein the diverted liquid flow bypasses the microscreen element; and
    defoaming the separated foam and bubbles at the upper region of the first filter element, wherein the liquid will not be exposed to the upper region of the first filter element if the liquid flow through the microscreen element does not become blocked.

19. The method of claim 18, further including the step of coating portions of the lower region of the first filter element with the defoaming agent.

* * * * *